United States Patent
Marunaka et al.

(10) Patent No.: US 9,693,857 B2
(45) Date of Patent: Jul. 4, 2017

(54) INTRAOCULAR LENS INSERTION APPARATUS

(75) Inventors: Akinori Marunaka, Chofu (JP); Toshihide Tanaka, Nagoya (JP); Yuji Nagura, Chofu (JP); Shuji Abe, Nagoya (JP)

(73) Assignee: Kowa Company, Ltd., Aichi (JP)

( * ) Notice: Subject to any disclaimer, the term of this patent is extended or adjusted under 35 U.S.C. 154(b) by 132 days.

(21) Appl. No.: 13/993,638

(22) PCT Filed: Dec. 1, 2011

(86) PCT No.: PCT/JP2011/077869
§ 371 (c)(1),
(2), (4) Date: Aug. 20, 2013

(87) PCT Pub. No.: WO2012/081421
PCT Pub. Date: Jun. 21, 2012

(65) Prior Publication Data
US 2013/0338676 A1   Dec. 19, 2013

(30) Foreign Application Priority Data

Dec. 14, 2010 (JP) ................................ 2010-278427

(51) Int. Cl.
*A61F 2/16* (2006.01)

(52) U.S. Cl.
CPC ............ *A61F 2/167* (2013.01); *A61F 2/1662* (2013.01); *A61F 2/1691* (2013.01); *A61F 2002/1682* (2015.04); *A61F 2002/16905* (2015.04)

(58) Field of Classification Search
CPC ...... A61F 2/1664; A61F 2/1662; A61F 2/167; A61F 2/1691; A61F 2/1678;

(Continued)

(56) References Cited

U.S. PATENT DOCUMENTS 4,706,666 A * 11/1987 Sheets .......................... 606/107
2004/0117012 A1* 6/2004 Vincent ........................ 623/6.12
(Continued)

FOREIGN PATENT DOCUMENTS

EP   2072025        6/2009
EP   2085053 A1     8/2009
(Continued)

OTHER PUBLICATIONS

Notification of Transmittal of Translation of the International Preliminary Report on Patentability (Form PCT/IB/338) in International App. No. PCT/JP2011/077869 mailed Jun. 20, 2013.
(Continued)

*Primary Examiner* — Eric Rosen
*Assistant Examiner* — Mikail Mannan
(74) *Attorney, Agent, or Firm* — Knobbe Martens Olson & Bear LLP

(57) ABSTRACT

Provided is technology which can prevent plunger deformation and further stabilize an intraocular lens insertion operation, even when an insertion tube section of an intraocular lens insertion apparatus has been further reduced in terms of the diameter thereof and has been made flatter. The intraocular lens insertion apparatus includes: a tip end region where a plunger comes into contact with an intraocular lens main body and an intraocular lens holding section; and a bar-shaped section extending from the rear end of this tip end region to the rear of the plunger. The bar-shaped section has a fixed thickness in the direction of the optical axis of the intraocular lens, and has an increasing thickness in a portion where the distance from the tip end of the tip end region is equal to or greater than a predetermined distance in a direction perpendicular to the optical axis direction and perpendicular to the plunger advancement direction.

16 Claims, 9 Drawing Sheets

(58) Field of Classification Search
CPC ...... A61F 2002/1681; A61F 2002/1682; A61F 2002/1683; A61F 2002/1686; A61F 2002/16902; A61F 2002/16903; A61F 2002/16905; A61F 2002/169051; A61F 2002/169052
USPC .................. 623/6.11, 6.12, 6.43; 606/107
See application file for complete search history.

(56) References Cited

U.S. PATENT DOCUMENTS

| | | | |
|---|---|---|---|
| 2009/0171365 A1* | 7/2009 | Tanaka | A61F 2/1664 606/107 |
| 2009/0171366 A1* | 7/2009 | Tanaka | 606/107 |
| 2010/0130985 A1 | 5/2010 | Tanaka | |
| 2011/0213380 A1 | 9/2011 | Han | |
| 2011/0224677 A1 | 9/2011 | Niwa et al. | |

FOREIGN PATENT DOCUMENTS

| | | |
|---|---|---|
| EP | 2161005 | 3/2010 |
| JP | 2008-061677 A | 3/2008 |
| JP | 2009-028223 A | 2/2009 |
| JP | 2009-160153 A | 7/2009 |
| JP | 2009-183367 A | 8/2009 |
| WO | WO 2010/032993 | 3/2010 |
| WO | 2010-064275 A1 | 6/2010 |
| WO | WO 2011061791 A1 * | 5/2011 |

OTHER PUBLICATIONS

Extended European Search Report dated Feb. 10, 2016 in corresponding European Patent Application No. 11848241.3.

* cited by examiner

FIG. 2
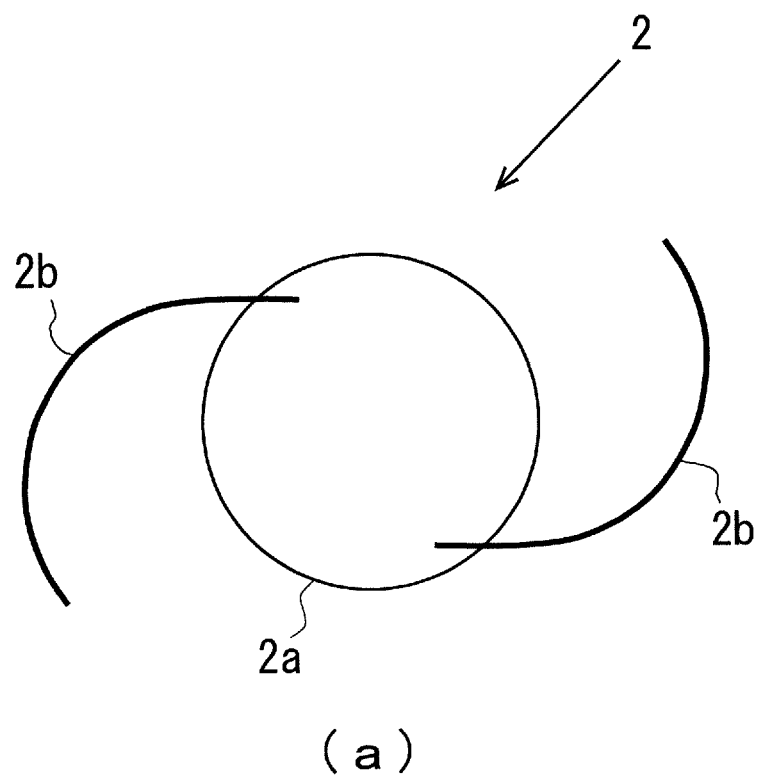
(a)
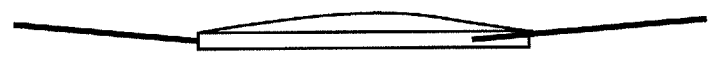
(b)

FIG. 4
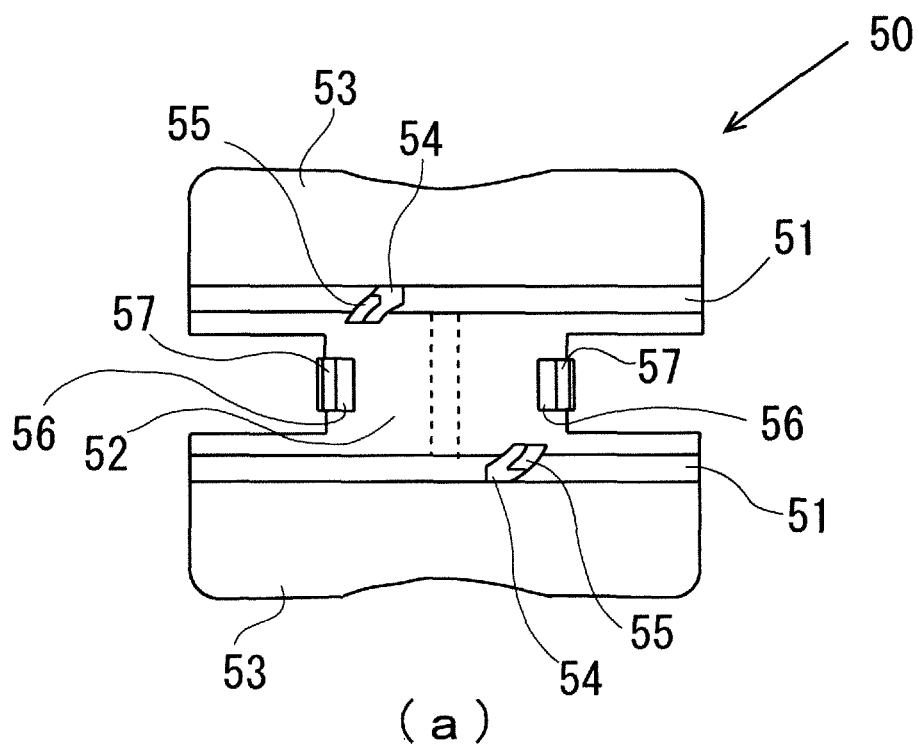
(a)
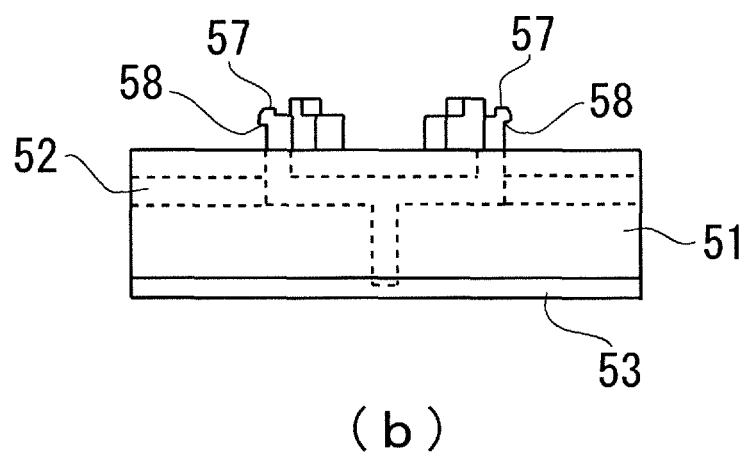
(b)

FIG. 6
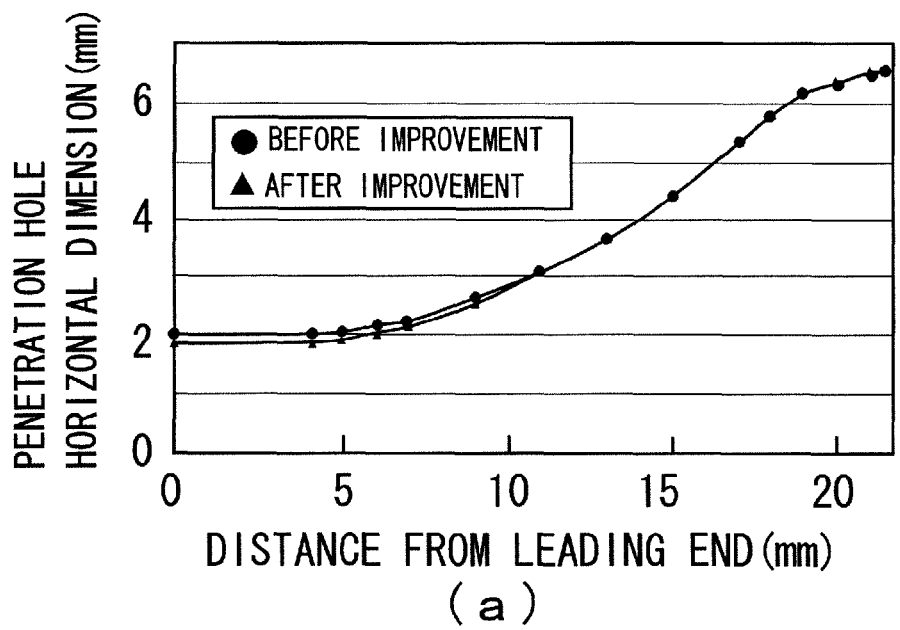
(a)
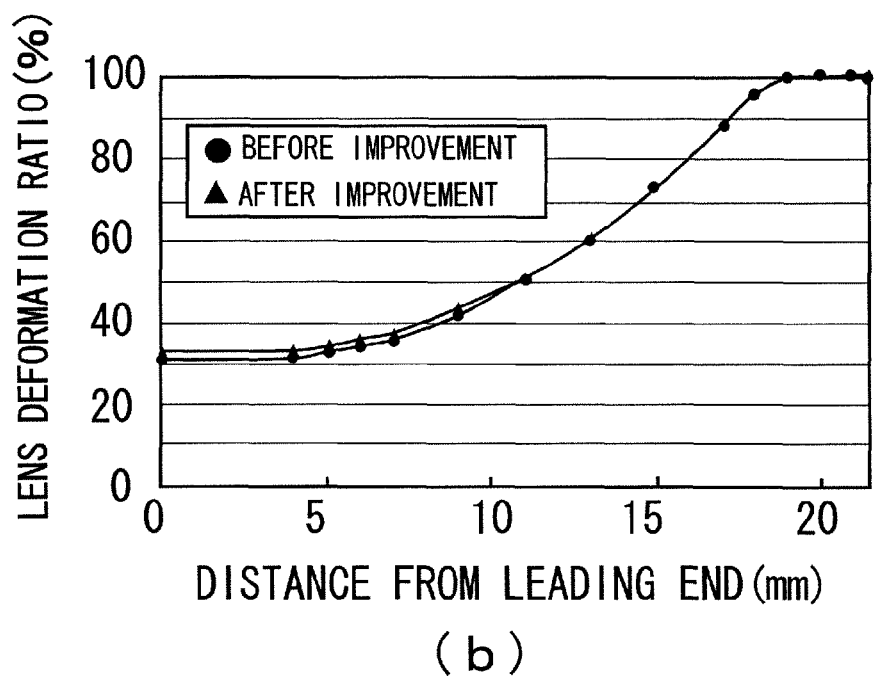
(b)

– 1 –
INTRAOCULAR LENS INSERTION APPARATUS

CROSS-REFERENCE TO RELATED APPLICATIONS

This application is the U.S. National Phase under 35 U.S.C. §371 of International Application PCT/JP2011/077869, filed Dec. 1, 2011, which was published in a non-English language, which claims priority to JP Application No. 2010-278427, filed Dec. 14, 2010.

TECHNICAL FIELD

The present invention relates to an intraocular lens insertion apparatus which is used to insert an intraocular lens into a patient's eyeball.

BACKGROUND ART

Hitherto, in a surgery such as cataract, a treatment is performed in which an incision is provided in an eye tissue such as a cornea (sclera) or an anterior lens capsule in an eyeball, a lens in a capsule is extracted and removed through the incision, and then an intraocular lens as a replacement for the lens is inserted from the incision into an eye so as to be disposed inside the capsule.

Particularly, in recent years, an insertion apparatus to be described below is used in many cases when inserting the intraocular lens from the incision into the eyeball. That is, the intraocular lens is inserted into the eyeball in a manner such that a leading end opening of an insertion tube provided in a leading end of the apparatus body is inserted into an eyeball through an incision and the intraocular lens is extruded by a rod-like plunger from the leading end opening of the insertion tube while being compactly deformed inside the apparatus body (for example, see Patent Literatures 1 to 3). Since such an insertion apparatus is used, the intraocular lens may be simply inserted into the eyeball using the incision provided to extract and remove the lens. For this reason, the surgery may be simplified and hence an occurrence of astigma or infection after the surgery may be suppressed.

Incidentally, in the operation of inserting the intraocular lens, there is a demand to further decrease the sizes of the incision and the leading end of the insertion tube in the insertion apparatus in order to reduce the patient's burden during the surgery. However, when the leading end of the insertion tube decreases in size, the diameter of the plunger needs to be decreased. Meanwhile, when the insertion tube decreases in size, the intraocular lens is compressed during the passage through the insertion tube, and hence there is a tendency that the resistance acting on the plunger during the extrusion becomes stronger. As a result, there is a case in which the plunger is deformed when extruding the intraocular lens from the insertion apparatus, so that the operation of inserting the intraocular lens is not stably performed.

CITATION LIST

Patent Literature

Patent Literature 1: Japanese Patent Application Laid-Open (JP-A) No. 2009-160153
Patent Literature 2: JP-A No. 2009-183367
Patent Literature 3: JP-A No. 2009-28223

SUMMARY OF INVENTION

Technical Problem

The invention is made in view of the above-described problems of the related art, and it is an object of the invention to provide a technique capable of further stabilizing an intraocular lens insertion operation by suppressing a deformation of a plunger when extruding an intraocular lens from an insertion apparatus even when an insertion tube of an intraocular lens insertion apparatus further decreases in size.

Solution to Problem

According to the invention, there is provided an intraocular lens insertion apparatus, wherein a plunger includes a leading end region which contacts an intraocular lens body or an intraocular lens holding portion and a rod-like portion which extends toward the rear side of the plunger from a trailing end of the leading end region, and wherein the rod-like portion is formed so that a thickness with respect to the optical axis direction of the intraocular lens is constant and a thickness of a portion distant from a leading end of the leading end region by a predetermined distance or more increases with respect to a direction perpendicular to the optical axis direction and perpendicular to the plunger advancing direction (the intraocular lens pressing direction).

More specifically, there is provided an intraocular lens insertion apparatus which inserts a deformable intraocular lens into an eyeball from an incision opening formed in an eyeball tissue, the intraocular lens insertion apparatus comprising:

an apparatus body which is formed in a substantially tubular shape and includes an insertion tube formed in a leading end thereof so as to be inserted into the incision opening;

an accommodation portion which is formed integrally with or separately from the apparatus body and accommodates the intraocular lens therein so as to dispose the intraocular lens inside the apparatus body; and a plunger which presses the intraocular lens accommodated in the accommodation portion by a leading end thereof so as to discharge the intraocular lens from the insertion tube into the eyeball, wherein the plunger includes a leading end region which contacts the intraocular lens body and/or a beard-like lens holding portion extending from the intraocular lens body, a rod-like portion which extends from a trailing end of the leading end region in a direction opposite to the pressing direction and a thin plate-like flat portion which is provided in the rod-like portion so as to be widened, and wherein the rod-like portion is formed so that, at a part of a region without the flat portion a thickness with respect to the optical axis direction of the accommodated intraocular lens is constant and a thickness of a portion distant from a leading end of the leading end region by a predetermined distance or more increases gradually with respect to a direction perpendicular to the optical axis direction and perpendicular to the pressing direction.

Here, when decreasing particularly the sizes of the insertion tube and the plunger of the apparatus body, there is a concern that the plunger may be deformed when extruding the intraocular lens into the eyeball as described above. Then, according to the careful examination of the inventor, the inventor found that the deformation mainly occurred so that the rod-like portion of the plunger was curved in a direction perpendicular to the optical axis of the intraocular lens. It is considered that this problem is caused by the fact that the intraocular lens body has a substantially round shape and easily rotates in a direction perpendicular to the optical axis.

Accordingly, in the invention, the dimension of the rod-like portion is made constant with respect to the optical axis direction of the accommodated intraocular lens, and the thickness of the portion distant from the leading end of the leading end region by a predetermined distance or more increases with respect to the direction perpendicular to the optical axis direction of the intraocular lens and perpendicular to the pressing direction. That is, even when a portion close to the leading end region in the rod-like portion decreases in diameter, a large load is not applied thereto. However, a large load may be applied to a portion distant from the leading end region when pressing the intraocular lens. In consideration of this state, only the portion distant from the leading end of the leading end region by a predetermined distance or more increases in thickness with respect to the direction perpendicular to the optical axis direction of the intraocular lens and perpendicular to the pressing direction.

Thus, since the thickness of the plunger may be increased with respect to the portion and the direction at minimum, an increase in the dimension of the plunger may be suppressed as minimal as possible on the whole. As a result, it is possible to decrease particularly the size of the insertion tube of the apparatus body and to suppress the deformation of the plunger. As a result, it is possible to further stably insert the intraocular lens into the eyeball through the smaller incision.

Further, in the invention, the predetermined distance may be equal to or longer than a distance in which the insertion tube may enter the eyeball. In the intraocular lens insertion apparatus, it is desirable to first decrease the size of at least the range of the insertion tube which may enter the eyeball. Thus, when the predetermined distance is set to be equal to or longer than the distance of the range in which the insertion tube may enter the eyeball, the small thickness of the rod-like portion of the plunger may be maintained in the range in which the insertion tube may enter the eyeball. With such a configuration, since the small diameter of the insertion tube may be maintained in the range in which the insertion tube may enter the eyeball, the incision may be also decreased in size as much as possible.

Further, in the invention, the plunger may be exposed from a leading end of the insertion tube by a predetermined exposure distance, and the predetermined distance may be equal to or longer than a sum of the exposure distance and a distance of a range in which the insertion tube is able to enter the eyeball. Then, even in a configuration in which the plunger may be exposed from the leading end of the insertion tube, it is possible to further reliably maintain the small diameter of the insertion tube in the range in which the insertion tube may enter the eyeball and hence to decrease the size of the incision as much as possible.

Further, in the invention, the predetermined distance may be equal to or longer than a length of the lens holding portion. Here, in the intraocular lens insertion apparatus, the lens holding portion of the intraocular lens is originally formed so as to contact the leading end region of the plunger. However, a case may be considered in which the lens holding portion is separated from the leading end region and also contacts the rod-like portion during the intraocular lens insertion operation. Thus, if the predetermined distance is set to be equal to or longer than the length of the lens holding portion, even when the lens holding portion is separated from the leading end region, the lens holding portion does not reach the thickness increasing portion of the rod-like portion. Accordingly, it is possible to suppress a problem in operation in which the lens holding portion is nipped between the rod-like portion and the apparatus body.

Further, in the invention, the rod-like portion may be provided with a tapered portion which is formed in a place distant from the leading end of the leading end region by the predetermined distance so that a thickness perpendicular to the optical axis direction and perpendicular to the pressing direction substantially increases in a linear manner depending on the distance from the leading end of the leading end region. That is, in a case of increasing the thickness of the portion distant from the leading end of the leading end region by a predetermined distance or more, when the thickness is increased in a stair shape, a stress concentrates on the portion, so that there is a risk that the portion may be intensively deformed. Thus, in the invention, in a case of increasing the thickness of the portion distant from the leading end of the leading end region by a predetermined distance or more, the thickness is gradually increased by forming the tapered portion. Accordingly, since the thickness of the rod-like portion may be increased without causing an unnecessary stress concentration therein, the deformation of the rod-like portion may be further reliably suppressed.

Further, in the invention, a bottom surface of the accommodation portion may be provided with two bank-like rails which are provided in parallel in the pressing direction of the plunger, and the plunger may be supported by two rails inside the apparatus body. By adopting this configuration, when the thickness of the rod-like portion increases, the rod-like portion moves in a direction in which the height of the rod-like portion supported by two rails increases. Then, for example, in a case where a slight clearance is provided at the upper side of the rod-like portion so as to form a position regulation guide, when the plunger is pressed toward the front side of the apparatus body by a certain degree, it is possible to decrease the clearance between the rod-like portion and the position regulation guide and hence to increase the plunger pressing resistance.

According to this configuration, it is possible to further reliably suppress the intraocular lens from carelessly popping out from the apparatus body by gradually increasing the plunger pressing resistance at the timing before extruding the intraocular lens from the insertion tube.

Furthermore, the above-described means for solving the problems of the invention may be used in combination as much as possible.

Advantageous Effects of Invention

According to the invention, even when the insertion tube of the intraocular lens insertion apparatus further decreases in size, it is possible to further stabilize the intraocular lens insertion operation by suppressing the deformation of the plunger when extruding the intraocular lens from the insertion apparatus.

BRIEF DESCRIPTION OF DRAWINGS

FIG. 2 is a diagram illustrating a schematic configuration of the intraocular lens of the embodiment of the invention.

FIG. 4 is a diagram illustrating a schematic configuration of a positioning member of the embodiment of the invention.

FIG. 6 is a graph with respect to a lens deformation ratio and a horizontal dimension of a penetration hole of the embodiment of the invention.

DESCRIPTION OF EMBODIMENTS

Figure 1:
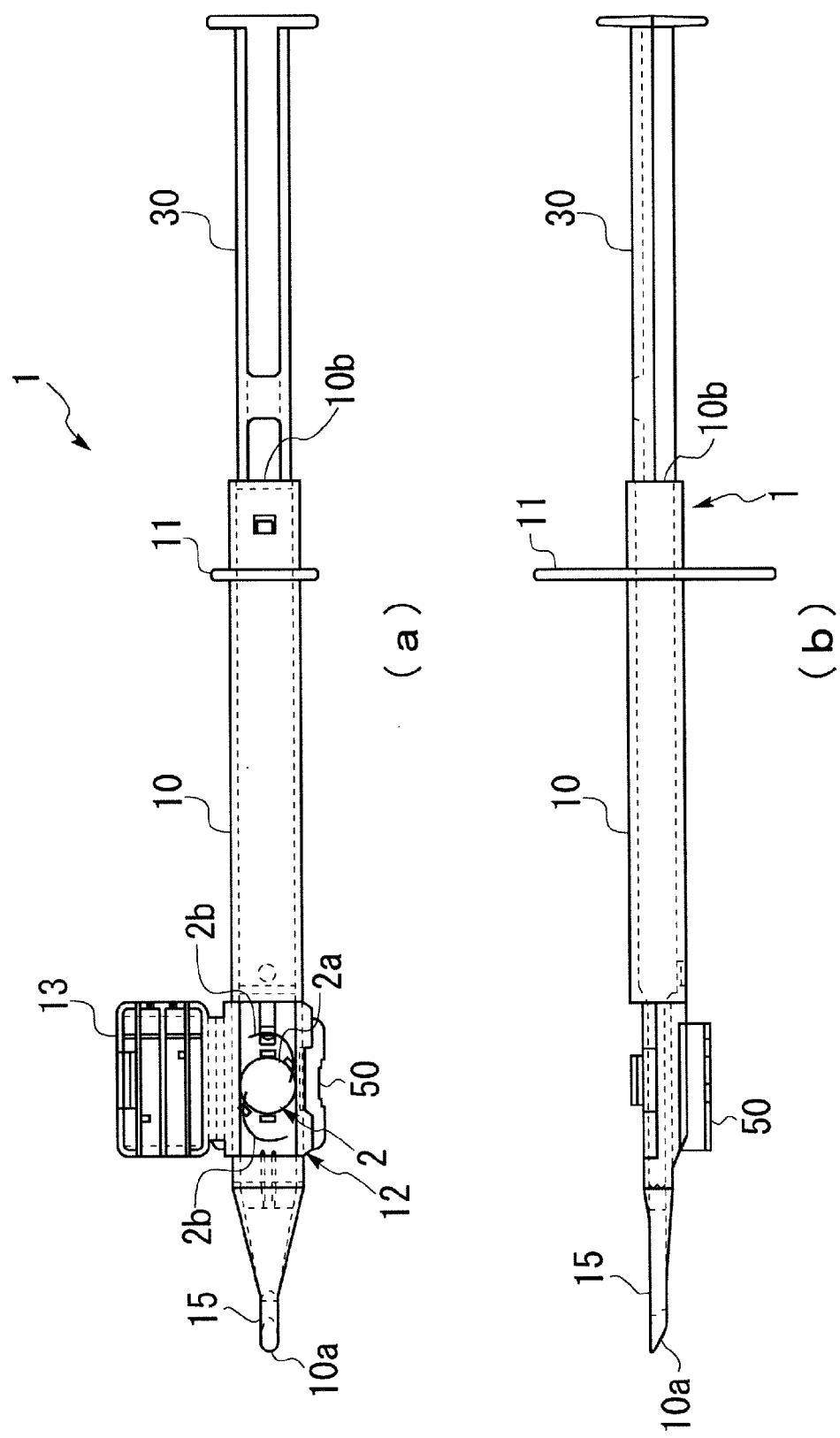
FIG. 1 is a diagram illustrating a schematic configuration of an intraocular lens insertion apparatus of Embodiment 1 of the invention.

Hereinafter, embodiments of the invention will be described by referring to the drawings.

Embodiment 1

FIG. 1 illustrates a schematic configuration of an intraocular lens insertion apparatus 1 (hereinafter, simply referred to as the insertion apparatus 1) of the embodiment. FIG. 1(a) illustrates a plan view and FIG. 1(b) illustrates a side view. The insertion apparatus 1 includes a nozzle body 10 that serves as an apparatus body which is formed with a cross-section having a substantially rectangular tube shape so that one side is largely opened (hereinafter, the largely opened side is referred to as a trailing end 10b) and the other side end is provided with a nozzle portion 15 as a thinly narrowed insertion tube and an obliquely opened leading end 10a and a plunger 30 which is inserted into the nozzle body 10 so as to move in a reciprocating manner. Furthermore, in the description below, the direction directed from the leading end 10a of the nozzle body 10 toward the trailing end 10b is set as the front to rear direction, the direction perpendicular to the drawing paper of FIG. 1 is set as the up to down direction, and the direction perpendicular to the front to rear direction and the up to down direction is set as the left to right direction.

The vicinity of the trailing end 10b of the nozzle body 10 is integrally provided with a hold portion 11 which projects in a plate shape and is used for a user to hold the hold portion by fingers when the plunger 30 is pressed toward the leading end of the nozzle body 10. Further, the nozzle body 10 which is positioned on the trailing end side of the nozzle portion 15 is provided with a stage portion 12 which serves as an accommodation portion used to set an intraocular lens 2 thereon. When a stage cover portion 13 is opened from the stage portion 12, the upside of the nozzle body 10 (the front side perpendicular to the drawing paper of FIG. 1(a)) is opened. Further, the stage portion 12 is mounted with a positioning member 50 from the downside of the nozzle body 10 (the rear side perpendicular to the drawing paper of FIG. 1(a)). By the positioning member 50, the intraocular lens 2 is stably held inside the stage portion 12 before the usage of the lens (during the carriage of the lens).

That is, in the insertion apparatus 1, the intraocular lens 2 is set on the stage portion 12 while the stage cover portion 13 is opened and the positioning member 50 is mounted to the stage portion 12 at the manufacturing process. Then, when the insertion apparatus is shipped and sold, a user separates the positioning member 50 while closing the stage cover portion 13, and then pushes the plunger 30 toward the leading end of the nozzle body 10, so that the intraocular lens 2 is pressed by the plunger 30 and the intraocular lens 2 is extruded from the leading end 10a.

FIG. 2 is a diagram illustrating a schematic configuration of the intraocular lens 2. FIG. 2(a) illustrates a plan view and FIG. 2(b) illustrates a side view. The intraocular lens 2 includes a lens body 2a which has a predetermined refractive power and two beard-like support portions 2b and 2b which are provided in the lens body 2a so as to hold the lens body 2a inside the eyeball. The support portions 2b and 2b correspond to the lens holding portion in the embodiment. The lens body 2a is formed of a flexible resin.

Figure 3:
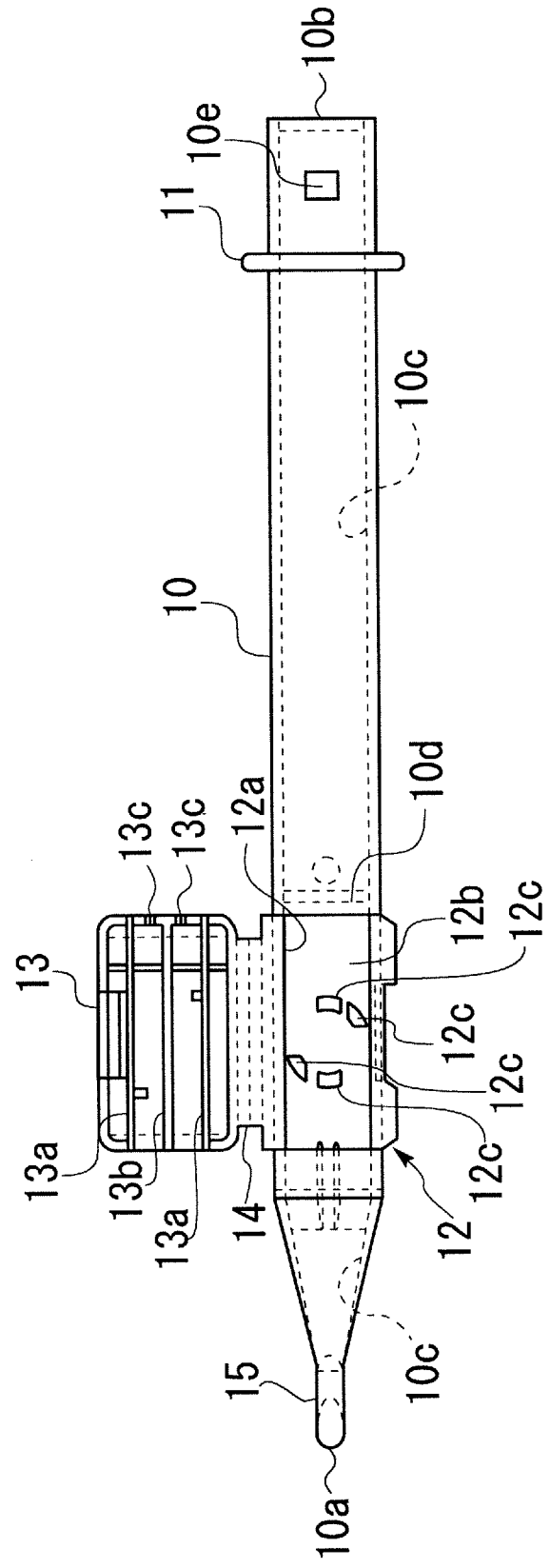
FIG. 3 is a diagram illustrating a schematic configuration of a nozzle body of Embodiment 1 of the invention.

FIG. 3 illustrates a plan view of the nozzle body 10. As described above, in the nozzle body 10, the intraocular lens 2 is set on the stage portion 12. Then, in this state, the intraocular lens 2 is pressed by the plunger 30 so as to be extruded from the leading end 10a. Furthermore, the nozzle body 10 is provided with a penetration hole 10c of which the cross-sectional shape changes in response to a change in the outer shape of the nozzle body 10. Then, when extruding the intraocular lens 2, the intraocular lens 2 is deformed in response to a change in the cross-sectional shape of the penetration hole 10c inside the nozzle body 10, and is deformed into a shape that the lens may be easily inserted into the incision formed in the patient's eyeball so as to be extruded.

The stage portion 12 is provided with a stage groove 12a which has a width slightly larger than the diameter of the lens body 2a of the intraocular lens 2. The dimension of the stage groove 12a in the front to rear direction is set to be larger than the maximum width including the support portions 2b and 2b extending toward both sides of the intraocular lens 2. Further, a set surface 12b is formed by the bottom surface of the stage groove 12a. The position of the set surface 12b in the up to down direction (the position in a direction perpendicular to the drawing paper of FIG. 3) is set to the upside in relation to the height position of the bottom surface of the penetration hole 10c of the nozzle body 10 (the front side in a direction perpendicular to the drawing paper of FIG. 3), and the set surface 12b is connected to the bottom surface of the penetration hole 10c by a bottom inclined surface 10d.

The stage portion 12 is integrally formed with the stage cover portion 13. The dimension of the stage cover portion 13 in the front to rear direction is equal to that of the stage portion 12. The stage cover portion 13 is connected by a thin plate-like connection portion 14 which is formed by extending the side surface of the stage portion 12 toward the stage cover portion 13. The connection portion 14 is formed so that the connection portion may be bent at the center thereof, and the stage cover portion 13 may cover the stage portion 12 from the upside thereof by bending the connection portion 14.

In the stage cover portion 13, the surface facing the set surface 12b when covering the stage portion is provided with ribs 13a and 13b which reinforce the stage cover portion 13 so as to stabilize the position of the intraocular lens 2. Further, a guide protrusion 13c is provided as the guide of the plunger 30.

The positioning member 50 is detachably mounted to the lower side of the set surface 12b of the stage portion 12. FIG. 4 illustrates a schematic configuration of the positioning member 50. FIG. 4(a) illustrates a plan view and FIG. 4(b) illustrates a side view. The positioning member 50 is formed separately from the nozzle body 10, and has a structure in which a pair of side wall portions 51 and 51 is connected by a connection portion 52. The lower ends of the respective side wall portions 51 are provided with holding portions 53 and 53 which extend outward.

Then, the upper ends of the respective side wall portions 51 and 51 are provided with a pair of first placement portions 54 and 54 which protrudes upward so as to have a circular-arc shape when viewed from the upside. Further, the outer peripheral side of the upper end surface of the first placement portion 54 is provided with first positioning portions 55 and 55 which are formed in a protruding manner. The distance between the inner diameters of the first positioning portions 55 is set to be slightly larger than the diameter of the lens body 2a of the intraocular lens 2.

Further, both ends of the connection portion 52 in the front to rear direction are provided with a pair of second placement portions 56 and 56 which protrude upward so as to have a rectangular shape when viewed from the upside. The height of the upper surface of the second placement portion 56 is set to be equal to the height of the upper surface of the first placement portion 54. Moreover, the outer portions of the upper surfaces of the second placement portions 56 and 56 are provided with second positioning portions 57 and 57 which protrude upward further throughout the left to right direction of the second placement portions 56. The gap between the inner surfaces of the second positioning portions 57 is set to be slightly larger than the diameter of the lens body 2a of the intraocular lens 2. Moreover, the upper end of the second placement portion 56 is provided with locking claws 58 and 58 which slightly protrude in the front to rear direction throughout the left to right direction.

In the embodiment, the positioning member 50 may be assembled from the downside of the set surface 12b of the nozzle body 10. The set surface 12b of the nozzle body 10 is provided with set surface penetration holes 12c which are formed so as to penetrate the set surface 12b in the thickness direction. The outer shape of the set surface penetration hole 12c is formed in a shape almost similar to the shapes of the first placement portion 54 and the second placement portion 56 of the positioning member 50 when viewed from the upside so as to be slightly larger than the shapes. Then, when the positioning member 50 is mounted to the nozzle body 10, the first placement portions 54 and 54 and the second placement portions 56 and 56 are inserted from the downside of the set surface 12b into the set surface penetration hole 12c so as to protrude toward the upside of the set surface 12b.

At this time, the locking claws 58 and 58 which are provided in the second placement portions 56 and 56 protrude toward the set surface 12b through the set surface penetration holes 12c and are locked to the upper surface of the set surface 12b. Accordingly, the positioning member 50 is assembled from the downside of the nozzle body 10, and the first placement portions 54 and 54 and the second placement portions 56 and 56 are fixed while protruding from the set surface 12b. Then, when setting the intraocular lens 2 to the set surface 12b, the bottom surface of the outer peripheral portion of the lens body 2a is placed on the upper surfaces of the first placement portions 54 and 54 and the second placement portions 56 and 56. Further, the position of the lens body 2a is regulated by the first positioning portions 55 and 55 and the second positioning portions 57 and 57 in the front to rear direction and the left to right direction.

Figure 5:
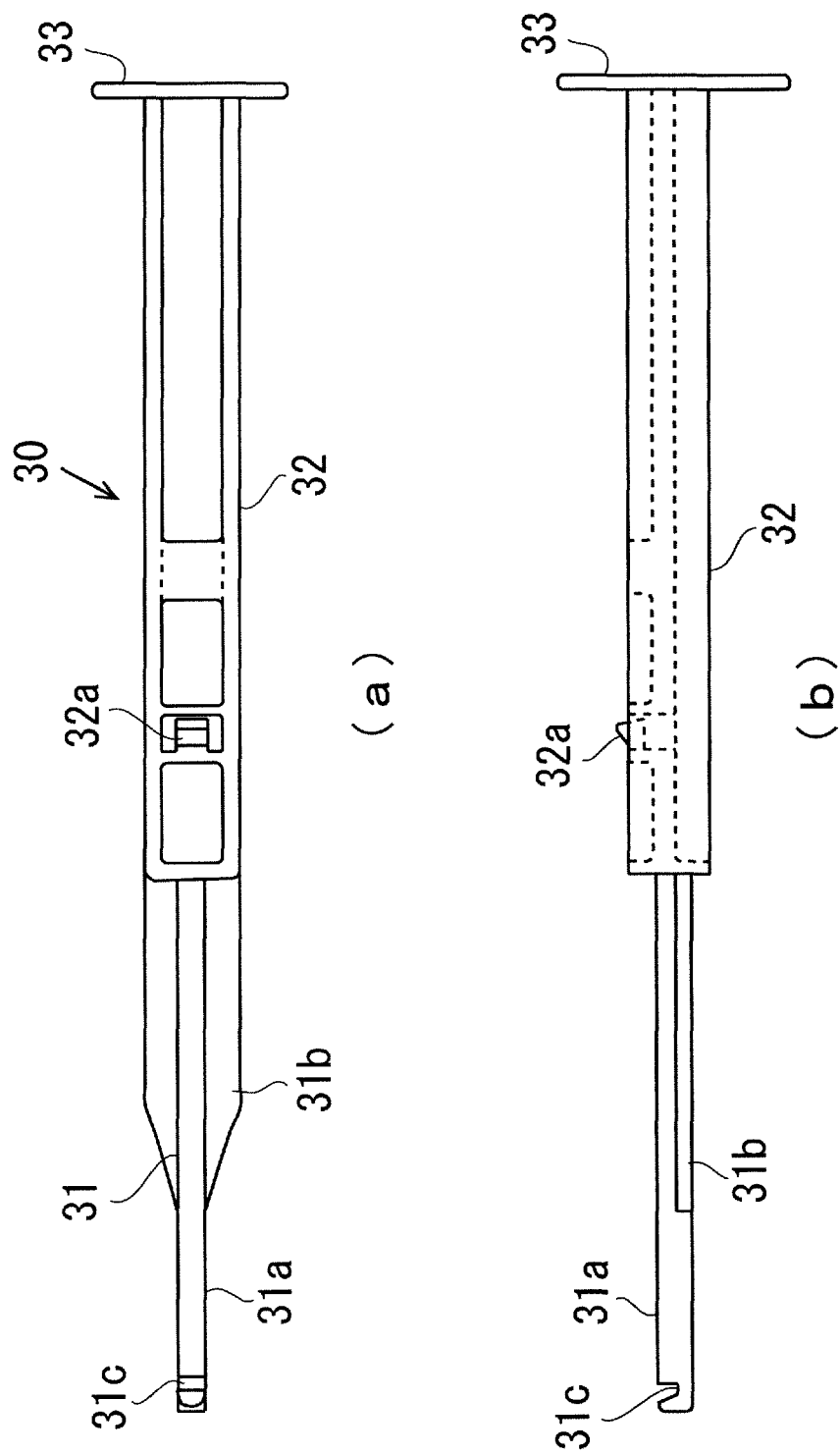
FIG. 5 is a diagram illustrating a schematic configuration of a plunger of the embodiment of the invention.

FIG. 5 illustrates a schematic configuration of the plunger 30. The plunger 30 has a length slightly larger than that of the nozzle body 10 in the front to rear direction. Then, the plunger includes a leading end side operation portion 31 which is basically formed in a columnar shape and a trailing end side insertion portion 32 which is basically formed in a rectangular rod shape. Then, the operation portion 31 includes a column portion 31a which is formed in a columnar shape and a thin plate-like flat portion 31b which is widened in the left to right direction of the column portion 31a.

The leading end of the operation portion 31 is provided with a notch 31c. As understood from FIG. 5, the notch 31c is formed in a groove shape which is opened toward the upside of the operation portion 31 and penetrates the operation portion in the left to right direction. Further, as understood from FIG. 5(b), the leading end side end surface of the notch 31c is formed as an inclined surface which faces the upside as it goes toward the leading end of the operation portion 31.

Meanwhile, the insertion portion 32 has a substantially H-shaped cross-section as a whole, and the dimensions thereof in the left to right direction and the up to down direction are set to be slightly smaller than those of the penetration hole 10c of the nozzle body 10. Further, the trailing end of the insertion portion 32 is provided with a disk-like pressure plate portion 33 which is widened in the up to down direction and the left to right direction.

The leading end side portion in relation to the center of the insertion portion 32 in the front to rear direction is provided with a claw 32a which protrudes toward the upside of the insertion portion 32 and is movable up and down by the elasticity of the material of the plunger 30. Then, when the plunger 30 is inserted into the nozzle body 10, the claw 32a engages with a locking hole 10e which is illustrated in FIG. 3 and is provided in the upper surface of the nozzle body 10 in the thickness direction, so that the relative position between the nozzle body 10 and the plunger 30 at the initial state is determined. Furthermore, the positions to be provided with the claw 32a and the locking hole 10e are set so that, in the engagement state, the leading end of the operation portion 31 is positioned behind the lens body 2a of the intraocular lens 2 set to the stage portion 12 and the support portion 2b behind the lens body 2a may be supported by the notch 31c from the downside.

Before using the insertion apparatus 1 with the above-described configuration, the plunger 30 is inserted into the nozzle body 10 so as to be disposed at the initial position. Further, the positioning member 50 is mounted to the nozzle body 10 from the downside of the set surface 12b as described above. Accordingly, the first placement portion 54 and the second placement portion 56 of the positioning member 50 are maintained so as to protrude toward the set surface 12b.

Further, the lens body 2a of the intraocular lens 2 is placed and positioned on the upper surfaces of the first placement portion 54 and the second placement portion 56 while the support portions 2b and 2b face the front to rear direction of the nozzle body 10. In this state, the intraocular lens 2 is supported without applying any load to the center thereof because the outer peripheral portion of the lens body 2a contacts the first placement portion 54 and the second placement portion 56. Further, in this state, the support portion 2b of the intraocular lens 2 is supported by the bottom surface of the notch 31c of the plunger 30.

Further, in this state, the second placement portion 56 is provided with a stopper which restricts the advancing movement of the plunger 30, and hence the plunger 30 may not advance as long as the positioning member 50 is not detached from the nozzle body 10.

In a case where the intraocular lens 2 is inserted into the patient's eyeball by using the insertion apparatus 1, the positioning member 50 is first separated from the nozzle body 10. Accordingly, the first placement portion 54 and the second placement portion 56 which support the lens body 2a of the intraocular lens 2 are retracted from the set surface 12b, so that the intraocular lens 2 is placed on the set surface 12b. Since the set surface 12b is formed as a flat surface, the intraocular lens 2 may be stably placed thereon. Further, since the width of the stage groove 12a is set to be slightly larger than the diameter of the lens body 2a of the intraocular lens 2, the rotation of the intraocular lens 2 in the circumferential direction on the set surface 12b is also suppressed.

Subsequently, the leading end 10a of the nozzle portion 15 of the nozzle body 10 is inserted into the incision provided in the eye tissue. Here, since the leading end 10a has an inclined opening shape, the leading end may be easily inserted into the incision. Then, the nozzle portion 15 is inserted into the incision. Subsequently, in this state, the pressure plate portion 33 of the plunger 30 is pressed toward the leading end of the nozzle body 10. Accordingly, the leading end of the operation portion 31 of the plunger 30 comes into contact with the outer periphery of the lens body 2a of the intraocular lens 2 set on the set surface 12b, and the intraocular lens 2 is guided toward the leading end 10a by the plunger 30.

With regard to the surgery in which the intraocular lens 2 is inserted into the patient's eyeball by using the above-described intraocular lens insertion apparatus 1, in recent years, there is a demand that the dimension in the vicinity of the leading end 10a of the nozzle body 10 needs to be decreased further and the diameter of the incision needs to be decreased in order to reduce the patient's burden. Specifically, there is an attempt to decrease the horizontal dimensions of the nozzle portion 15 and the penetration hole 10c by about 0.1 mm.

FIG. 6 illustrates a graph with respect to the lens deformation ratio and the horizontal dimension of the penetration hole 10c before and after performing the above-described improvement (a decrease in dimension). FIG. 6(a) illustrates an example of a relation of the distance from the leading end 10a to the penetration hole 10c and the horizontal dimension of the penetration hole 10c before and after the improvement. The horizontal axis indicates the distance from the leading end 10a and the vertical axis indicates the horizontal dimension of the penetration hole 10c. Further, FIG. 6(b) illustrates an example of a relation between the lens deformation ratio and the distance from the leading end 10a before and after the improvement. The horizontal axis indicates the distance from the leading end 10a and the vertical axis indicates the lens deformation ratio. As apparently understood from FIGS. 6(a) and 6(b), the horizontal dimension of the penetration hole 10c decreases in the vicinity of the leading end 10a, so that the lens deformation ratio increases.

In a case where this improvement is performed, when the intraocular lens 2 is pressed by the plunger 30 so as to move forward inside the nozzle body 10, the deformation ratio of the intraocular lens 2 further increases, so that the resistance against the pressing operation of the plunger 30 further increases. Further, there is a need to decrease the diameter of the operation portion 31 of the plunger 30 in accordance with a decrease in the size of the penetration hole 10c. As a result, since the operation portion 31 of the plunger 30 is thin, there is a concern that deformation such as bending of the operation portion 31 occurs. Then, it is difficult to accurately transmit the movement of the plunger 30 to the intraocular lens 2, and hence there is a case in which the intraocular lens 2 may not be easily and stably inserted into the patient's eyeball.

When extruding the intraocular lens 2 from the leading end 10a of the nozzle body 10, the intraocular lens is extruded in a deformed state. For this reason, there is a concern that a problem may occur in which the intraocular lens 2 pops out due to the elastic force generated when restoring the shape of the intraocular lens 2, and hence it is important to stably control the plunger 30 during the extrusion. Thus, it is desirable that the deformation of the operation portion 31 of the plunger 30 is as small as possible.

Furthermore, since the lens body 2a of the intraocular lens 2 has a substantially disk shape, the lens body 2a may easily rotate inside the nozzle body 10 about the optical axis when the intraocular lens 2 is pressed by the plunger 30. Thus, in many cases, the deformation direction of the operation portion 31 of the plunger 30 is the horizontal direction. On the contrary, in the embodiment, the horizontal width is set to be larger than the vertical width in rear of a predetermined place of the column portion 31a of the operation portion 31, so that the curving of the operation portion 31 is suppressed.

Figure 7:
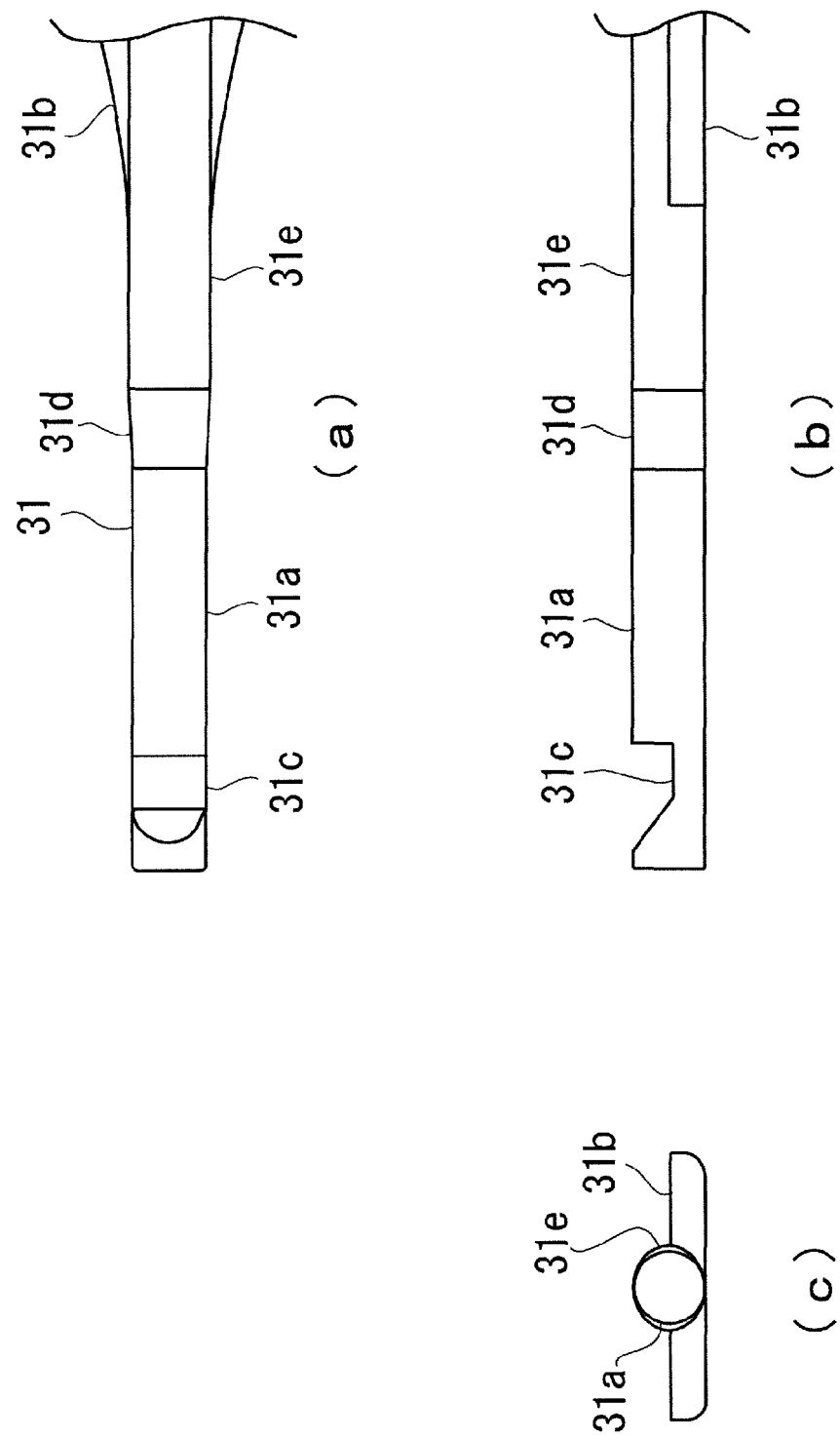
FIG. 7 is a diagram illustrating the vicinity of a leading end of the plunger of the embodiment of the invention.

FIG. 7 illustrates a specific configuration of the operation portion 31 of the plunger 30 of the embodiment. FIG. 7(a) is a diagram when viewed from the upside, FIG. 7(b) is a diagram when viewed from the left to right direction, and FIG. 7(c) is a diagram when viewed from the leading end direction. In the embodiment, a tapered portion 31d is provided at the center of the column portion 31a in the front to rear direction, and an elongated column portion 31e is provided by increasing the horizontal width of the column portion 31a at the rear side of the tapered portion 31d.

In other words, the vertical dimensions of the column portion 31a, the tapered portion 31d, and the elongated column portion 31e of the operation portion 31 are set to be constant, and only the horizontal dimensions thereof are increased in the middle of the operation portion. Thus, since only the dimension in a direction in which the operation portion 31 is easily deformed increases, it is possible to further efficiently suppress the deformation of the operation portion 31 and to suppress the increase amount in dimension as minimal as possible. Further, since the direction of increasing the dimension of the operation portion 31 is set to only the left to right direction, the structure in the up to down direction is simplified, and hence the structure of the plunger 30 may be totally simplified. Furthermore, since the direction of highly precisely managing the dimension may be limited to the left to right direction, it is possible to simplify the mold manufacturing process and the product dimension management. Furthermore, in the operation portion 31 of FIG. 7, the notch 31c and the leading end side portion of the notch 31c correspond to the leading end region. The column portion 31a at the trailing end side of the notch 31c, the tapered portion 31d, and the elongated column portion 31e correspond to a rod-like portion.

Here, in FIG. 7, it is desirable to set the distance from the leading end of the operation portion 31 to the tapered portion 31d to be equal to or longer than the length in the front to rear direction of the range in which the leading end 10a of the nozzle body 10 is inserted into the patient's eyeball. For example, when a mark representing the insertion range is present in the nozzle portion 15 of the nozzle body 10, the distance may be set to be equal to or longer than the distance from the leading end 10a to the mark. In this way, the dimension of the operation portion 31 may be suppressed in the insertion range inside the patient's eyeball, and hence the horizontal dimension of the portion inserted into the patient's eyeball in the nozzle body 10 may be suppressed as small as possible. Accordingly, it is possible to further suppress the size of the incision provided in the patient's eye tissue as small as possible.

Furthermore, in the operation of inserting the intraocular lens 2, in a case where the plunger 30 may protrude (be exposed) from the leading end 10a of the nozzle body 10, the distance from the leading end of the operation portion 31 to the tapered portion 31d may be set to be equal to or longer than the sum of the protruding (exposing) length of the plunger 30 and the length of the insertion range of the leading end 10a of the nozzle body 10 inside the patient's eyeball. Then, even in a configuration in which the plunger 30 may protrude (be exposed) from the leading end 10a of the nozzle body 10, the horizontal dimension of the portion inserted into the patient's eyeball in the nozzle body 10 may be further reliably suppressed as small as possible.

Moreover, the distance from the leading end of the operation portion 31 to the tapered portion 31d may be set to be equal to or longer than the length of the support portion 2b of the intraocular lens 2. Here, the support portion 2b of the intraocular lens 2 is supported by the bottom surface of the notch 31c of the plunger 30. However, when pressing the intraocular lens 2 by the plunger 30 in the operation of inserting the intraocular lens 2, there is a case in which the support portion 2b is separated from the notch 31c. In this case, there is a concern that the support portion 2b is nipped between the plunger 30 and the nozzle body 10, so that the plunger 30 may not easily move.

On the contrary, when the distance from the leading end of the operation portion 31 to the tapered portion 31d is set to be equal to or longer than the length of the support portion 2b of the intraocular lens 2, the support portion 2b does not reach the tapered portion 31d if the support portion 2b is separated from the notch 31c. Accordingly, it is possible to suppress a problem in operation in which the support portion 2b is nipped between the plunger 30 and the nozzle body 10.

Furthermore, in the above-described embodiment, the distance from the leading end of the operation portion 31 to the tapered portion 31d corresponds to a predetermined distance. Further, in the above-described embodiment, the horizontal dimension of the operation portion 31 is increased by providing the tapered portion 31d in the operation portion 31. However, the method of increasing the horizontal dimension of the operation portion 31 is not limited to the above-described example. For example, the same effect may be substantially obtained even when increasing the dimension by a step shape, a stair shape, and a curved surface shape.

Embodiment 2

Next, Embodiment 2 of the invention will be described. Even in the embodiment, as described in Embodiment 1, a configuration is employed in which the operation portion 31 of the plunger 30 is provided with the tapered portion 31d so as to increase only the horizontal dimension at the elongated column portion 31e. Then, in the embodiment, in addition to this configuration, the plunger 30 is supported by two rails at the bottom surface of the penetration hole of the apparatus body. Hereinafter, this embodiment will be described.

Figure 8:
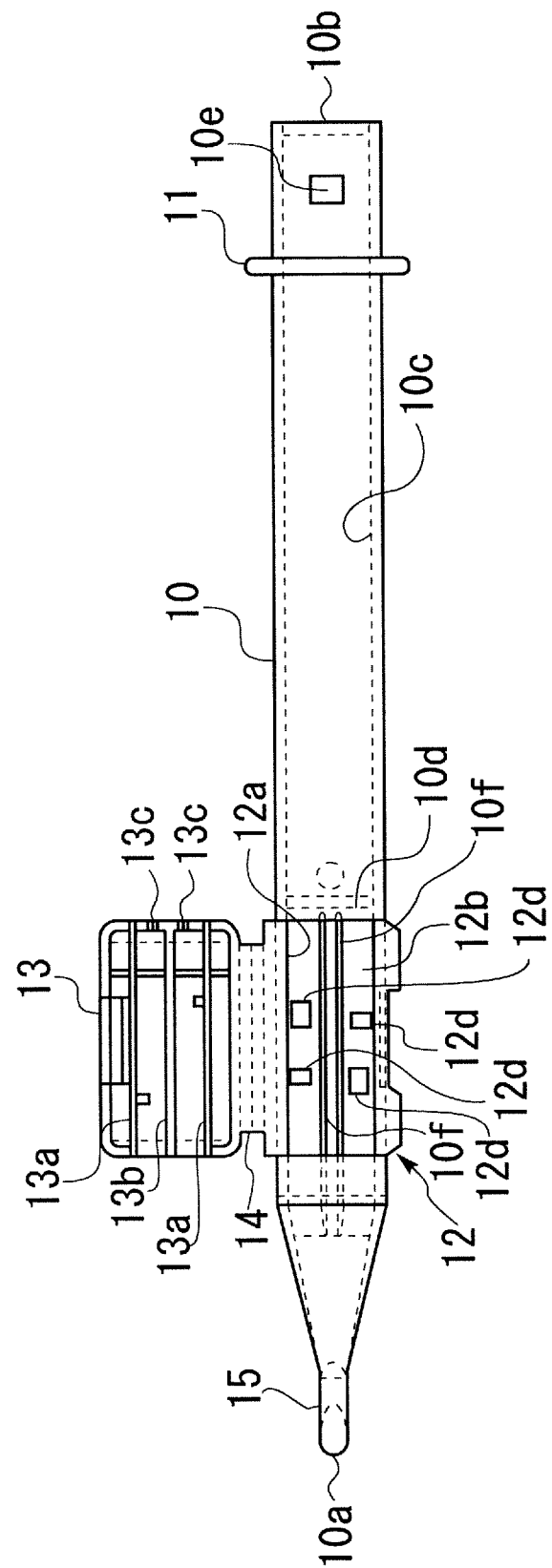
FIG. 8 is a diagram illustrating a schematic configuration of a nozzle body of Embodiment 2 of the invention.

FIG. 8 illustrates the nozzle body 10 according to the embodiment. The nozzle body 10 according to the embodiment is different from that of Embodiment 1 in that the operation portion 31 of the plunger 30 is supported by two rails 10f and 10f in the set surface 12b of the stage portion 12. Further, as illustrated in FIG. 8, a set surface penetration hole 12d is provided so as to be disposed differently from the set surface penetration hole 12c of Embodiment 1. This is because a space for providing the rails 10f and 10f needs to be ensured in the set surface 12b.

Figure 9:
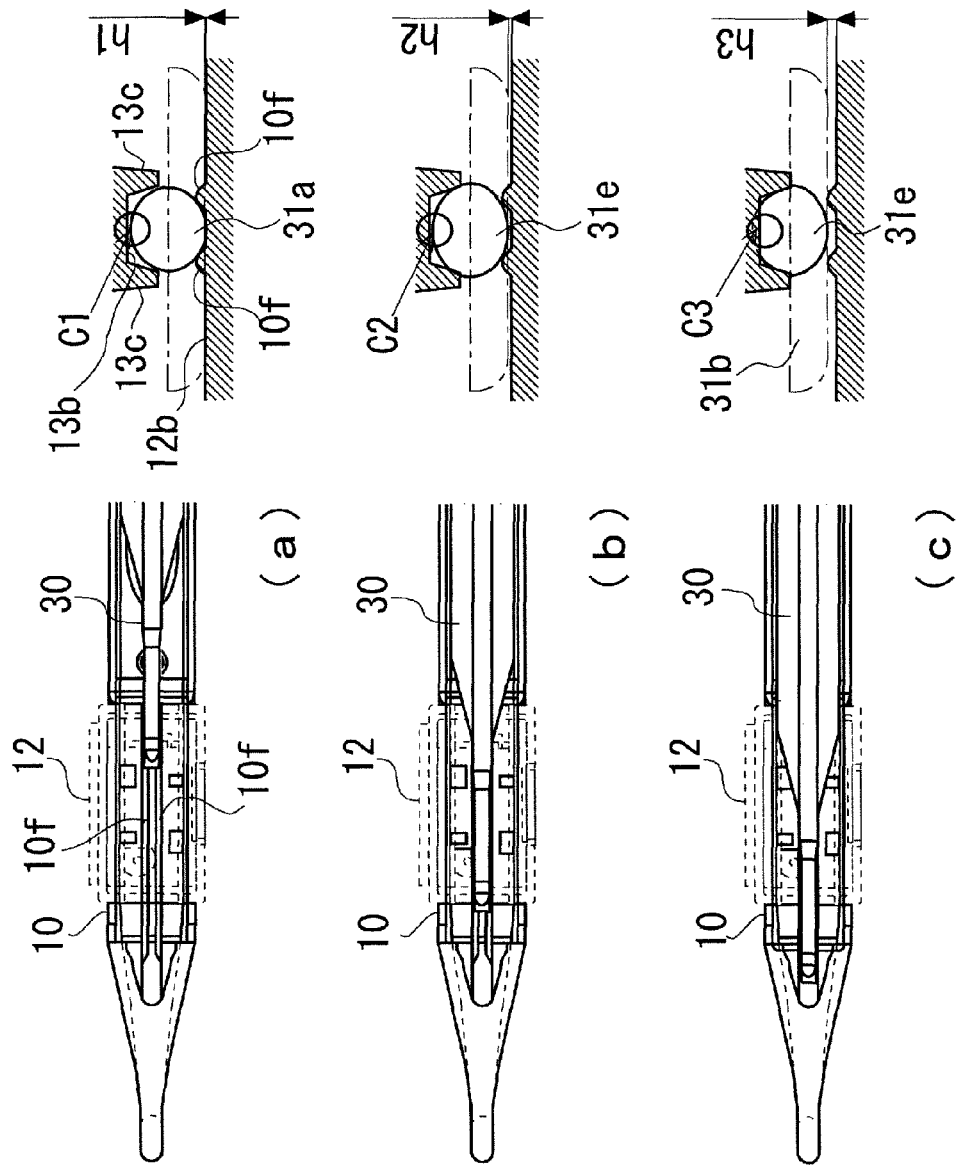
FIG. 9 is a diagram illustrating a relation between a height and a position of a plunger of Embodiment 2 of the invention.

FIG. 9 illustrates an operation in which the plunger 30 of the embodiment is pressed toward the leading end of the nozzle body 10 so as to extrude the intraocular lens 2. FIG. 9(a) illustrates a state where the plunger 30 is present at the initial position, FIG. 9(b) illustrates a state where the leading end of the operation portion 31 of the plunger 30 has passed through the stage portion 12, and FIG. 9(c) illustrates a state where a flat portion 31b of the plunger 30 reaches the stage portion 12 and the flat portion 31b is supported by two rails 10f and 10f. Further, in FIGS. 9(a) to 9(c), the left drawings represent the top views, and the right drawings represent the cross-sectional views of the operation portion 31 which is supported by two rails 10f and 10f.

Furthermore, as illustrated in the right drawings of FIGS. 9(a) to 9(c), the operation portion 31 of the plunger 30 is supported by two rails 10f and 10f from the downside and the position of the upper side thereof is regulated by the guide protrusions 13c and 13c and the rib 13b in a state where the stage cover portion 13 is closed. Furthermore, in the left drawings of FIGS. 9(a) to 9(c), the configuration of the stage cover portion 13 is indicated by the thin chain line in order to easily understand the operation of the plunger 30.

In FIG. 9(a), the column portion 31a of the operation portion 31 is supported by the inner inclined surfaces of the rails 10f and 10f. In this case, the height of the lower end of the column portion 31a from the set surface 12b becomes "h1". Further, the position of the upper side of the column portion 31a is regulated by the guide protrusions 13c and 13c and the rib 13b. However, since the horizontal dimension of the column portion 31a is equal to the vertical dimension thereof, the clearance C1 between the column portion 31a and the rib 13b is comparatively large. In this state, the operation resistance of the plunger 30 is very small, and hence the operation of pressing the intraocular lens 2 may be smoothly performed.

In FIG. 9(b), the lower side of the elongated column portion 31e is supported by the inner inclined surfaces of the rails 10f and 10f, and the position of the upper side of the elongated column portion 31e is regulated by the guide protrusions 13c and 13c and the rib 13b. In this state, since the horizontal dimension of the elongated column portion 31e is longer than the horizontal dimension of the column portion 31a, the height of the lower side of the elongated column portion 31e from the set surface 12b becomes "h2" higher than that of FIG. 9(a). Since the vertical dimension of the elongated column portion 31e is equal to that of the column portion 31a, the clearance C2 between the rib 13b and the upper side of the elongated column portion 31e is smaller than that of the state illustrated in FIG. 9(a). As a result, in the state of FIG. 9(b), the operation resistance of the plunger 30 increases compared to the state of FIG. 9(a).

In FIG. 9(c), the flat portion 31b is supported by the apexes of the rails 10f and 10f and the position of the upper side of the elongated column portion 31e is regulated by the guide protrusions 13c and 13c and the rib 13b. In this state, since the flat portion 31b is placed on the rails 10f and 10f, the height of the elongated column portion 31e from the lower set surface 12b becomes the higher height "h3". In this case, the clearance between the rib 13b and the upper side of the elongated column portion 31e becomes a minus value C3, so that interference between the elongated column portion 31e and the rib 13b occurs. Thus, in this state, the operation resistance of the plunger 30 further increases.

As described above, in the embodiment, only the horizontal dimension is halfway increased by providing the tapered portion 31d in the operation portion 31 of the plunger 30, and the plunger 30 is supported by two rails 10f and 10f at the stage portion 12 of the nozzle body 10. Thus, the operation resistance of the plunger 30 increases as the plunger 30 is gradually pressed toward the leading end of the nozzle body 10, so that the operation of the plunger 30 immediately before extruding the intraocular lens 2 from the nozzle body 10 may be further stabilized. As a result, it is possible to further reliably suppress a problem in which the intraocular lens 2 carelessly pops out from the nozzle body 10 into the eyeball.

REFERENCE SIGNS LIST 1 insertion apparatus
2 intraocular lens
10 apparatus body
10a leading end
10b trailing end
10f rail
12 stage portion
12b set surface
13 stage cover portion
13a rib
13b rib
13c guide protrusion
30 plunger
31 operation portion
31a column portion
31b flat portion
31d tapered portion
31e elongated column portion
50 positioning member

What is claimed is:

1. An intraocular lens insertion apparatus which inserts a deformable intraocular lens into an eyeball from an incision opening formed in an eyeball tissue, the intraocular lens insertion apparatus comprising:
   an apparatus body which is formed in a substantially tubular shape and includes an insertion tube formed in a leading end thereof so as to be inserted into the incision opening;
   an accommodation portion which is formed integrally with or separately from the apparatus body and accommodates the intraocular lens therein so as to dispose the intraocular lens inside the apparatus body; and
   a plunger which presses the intraocular lens accommodated in the accommodation portion by a leading end of the plunger so as to discharge the intraocular lens from the insertion tube into the eyeball,
   wherein the leading end of the plunger contacts the intraocular lens body and/or a lens holding portion having an elongate curved shape and extending from the intraocular lens body and, wherein the plunger includes:
      a columnar portion which extends from a trailing end of the leading end in a direction opposite to a pressing direction and is formed in a columnar shape, and
      a flat portion which is provided on the columnar portion so as to be widened, the flat portion further comprising a taper-shaped area with a width in a first direction perpendicular to an optical axis direction and perpendicular to the pressing direction, wherein the width of the taper-shaped area increases along the direction opposite to the pressing direction, wherein the taper-shaped area has a constant thickness in the optical axis direction, and
   wherein the columnar portion comprises a first portion having a first constant cross-sectional width in the first direction, an elongate portion having a second constant cross-sectional width greater than the first cross-sectional width in the first direction, and a tapered portion connecting the first portion and the elongate portion, the tapered portion having a cross-sectional width in the first direction that gradually increases from the first cross-sectional width to the second cross-sectional width and is distal to the flat portion,
   wherein a thickness of the first portion, the elongate portion and the tapered portion in the optical axis direction is constant.

2. The intraocular lens insertion apparatus according to claim 1, wherein a length of the first portion of the columnar portion is equal to or longer than a distance of a range in which the insertion tube is able to enter the eyeball.

3. The intraocular lens insertion apparatus according to claim 2, wherein the cross-sectional width in the first direction of the tapered portion of the columnar portion increases in a linear manner along the direction opposite to the pressing direction.

4. The intraocular lens insertion apparatus according to claim 3, wherein a bottom surface of the accommodation portion is provided with two bank-like rails which are provided in parallel in the pressing direction of the plunger, and
   wherein the plunger is supported by the two bank-like rails inside the apparatus body.

5. The intraocular lens insertion apparatus according to claim 2, wherein a bottom surface of the accommodation portion is provided with two bank-like rails which are provided in parallel in the pressing direction of the plunger, and
   wherein the plunger is supported by the two bank-like rails inside the apparatus body.

6. The intraocular lens insertion apparatus according to claim 1, wherein the plunger is able to be exposed from a leading end of the insertion tube by a predetermined exposure distance, and
   wherein a length of the first portion of the columnar portion is equal to or longer than a sum of the exposure distance and a distance of a range in which the insertion tube is able to enter the eyeball.

7. The intraocular lens insertion apparatus according to claim 6, wherein the cross-sectional width in the first direction of the tapered portion of the columnar portion increases in a linear manner along the direction opposite to the pressing direction.

8. The intraocular lens insertion apparatus according to claim 7, wherein a bottom surface of the accommodation portion is provided with two bank-like rails which are provided in parallel in the pressing direction of the plunger, and
   wherein the plunger is supported by the two bank-like rails inside the apparatus body.

9. The intraocular lens insertion apparatus according to claim 6, wherein a bottom surface of the accommodation portion is provided with two bank-like rails which are provided in parallel in the pressing direction of the plunger, and wherein the plunger is supported by the two bank-like rails inside the apparatus body.

10. The intraocular lens insertion apparatus according to claim 1, wherein a length of the first portion of the columnar portion is equal to or longer than a length of the lens holding portion.

11. The intraocular lens insertion apparatus according to claim 10, wherein the cross-sectional width in the first direction of the tapered portion of the columnar portion increases in a linear manner along the direction opposite to the pressing direction.

12. The intraocular lens insertion apparatus according to claim 11, wherein a bottom surface of the accommodation portion is provided with two bank-like rails which are provided in parallel in the pressing direction of the plunger, and wherein the plunger is supported by the two bank-like rails inside the apparatus body.

13. The intraocular lens insertion apparatus according to claim 10, wherein a bottom surface of the accommodation portion is provided with two bank-like rails which are provided in parallel in the pressing direction of the plunger, and wherein the plunger is supported by the two bank-like rails inside the apparatus body.

14. The intraocular lens insertion apparatus according to claim 1, wherein the cross-sectional width in the first direction of the tapered portion of the columnar portion increases in a linear manner along the direction opposite to the pressing direction.

15. The intraocular lens insertion apparatus according to claim 14, wherein a bottom surface of the accommodation portion is provided with two bank-like rails which are provided in parallel in the pressing direction of the plunger, and wherein the plunger is supported by the two bank-like rails inside the apparatus body.

16. The intraocular lens insertion apparatus according to claim 1, wherein a bottom surface of the accommodation portion is provided with two bank-like rails which are provided in parallel in the pressing direction of the plunger, and wherein the plunger is supported by the two bank-like rails inside the apparatus body.

* * * * *